(12) United States Patent
Justis (10) Patent No.: US 8,211,149 B2
(45) Date of Patent: Jul. 3, 2012

(54) ELONGATED MEMBERS WITH EXPANSION CHAMBERS FOR TREATING BONY MEMBERS

(75) Inventor: Jeff R. Justis, Memphis, TN (US)

(73) Assignee: Warsaw Orthopedic, Warsaw, IN (US)

(*) Notice: Subject to any disclaimer, the term of this patent is extended or adjusted under 35 U.S.C. 154(b) by 1022 days.

(21) Appl. No.: 12/119,003

(22) Filed: May 12, 2008

(65) Prior Publication Data
US 2009/0281542 A1 Nov. 12, 2009

(51) Int. Cl.
*A61B 17/70* (2006.01)
(52) U.S. Cl. ........ 606/258; 606/57; 606/105; 623/17.12
(58) Field of Classification Search .............. 606/53–63, 606/86 R, 90, 246–279; 600/201–246; 623/17.11–17.116; 464/26
See application file for complete search history.

(56) References Cited

U.S. PATENT DOCUMENTS

| | | | |
|---|---|---|---|
| 4,854,304 A | 8/1989 | Zielke | |
| 4,998,936 A | 3/1991 | Mehdian | |
| 5,356,411 A * | 10/1994 | Spievack | 606/63 |
| 5,466,261 A * | 11/1995 | Richelsoph | 623/23.47 |
| 5,536,269 A | 7/1996 | Spievack | |
| 5,626,581 A * | 5/1997 | Staehlin et al. | 606/63 |
| 5,700,263 A | 12/1997 | Schendel | |
| 5,702,389 A | 12/1997 | Taylor et al. | |
| 5,723,013 A | 3/1998 | Jeanson et al. | |
| 6,036,690 A * | 3/2000 | De La Plaza Fernandez | 606/53 |
| 6,106,525 A * | 8/2000 | Sachse | 606/59 |
| 6,277,124 B1 | 8/2001 | Haag | |
| 6,358,283 B1 | 3/2002 | Hogfors et al. | |
| 6,514,255 B1 | 2/2003 | Ferree | |
| 6,565,576 B1 | 5/2003 | Stauch et al. | |
| 6,616,669 B2 | 9/2003 | Ogilvie et al. | |
| 6,673,079 B1 | 1/2004 | Kane | |
| 6,796,984 B2 * | 9/2004 | Soubeiran | 606/300 |
| 6,835,207 B2 | 12/2004 | Zacouto et al. | |
| 6,918,910 B2 | 7/2005 | Smith et al. | |
| 7,066,957 B2 | 6/2006 | Graf | |
| 2003/0055427 A1 | 3/2003 | Graf | |
| 2004/0006341 A1 | 1/2004 | Shaolian et al. | |
| 2004/0153067 A1 * | 8/2004 | Smith et al. | 606/60 |
| 2005/0234448 A1 | 10/2005 | McCarthy | |
| 2006/0009767 A1 | 1/2006 | Kiester | |
| 2006/0084994 A1 | 4/2006 | Atkinson et al. | |
| 2006/0085703 A1 | 4/2006 | Lee | |
| 2006/0155279 A1 | 7/2006 | Ogilvie | |
| 2007/0191846 A1 | 8/2007 | Bruneau et al. | |
| 2007/0276368 A1 | 11/2007 | Trieu et al. | |
| 2007/0276369 A1 | 11/2007 | Allard et al. | |
| 2008/0045951 A1 | 2/2008 | Fanger et al. | |
| 2008/0097441 A1 | 4/2008 | Hayes et al. | |
| 2008/0172063 A1 * | 7/2008 | Taylor | 606/105 |

OTHER PUBLICATIONS

International Searching Authority, ISR and Written Opinion, Dec. 17, 2009. "PS Medical® Flow Control Products—Shunts." Medtronic, Inc. website. http://www.medtronic.com/neurosurgery/shunts.html. Medtronic, Inc. Minneapolis, Minnesota, USA.
Adam Gruca, "The Journal of Bone & Joint Surgery." the Pathogenesis and Treatment of Idiopathic Scoliosis: A Preliminary Report, J Bone Joint Surg Am. 1958; 40: 570-584, The Journal of Bone and Joint Surgery, Needham, MA www.jbjs.org.

* cited by examiner

*Primary Examiner* — Eduardo C Robert
*Assistant Examiner* — Michelle C Eckman (57) ABSTRACT

The present application is directed to devices with expandable lengths for treating bony members. The device may include an elongated member with two sections that are movable relative to each other. An expansion chamber may be positioned between the first and second sections. A pump may move fluid from a reservoir and through a conduit into the expansion chamber. The expansion chamber expands upon receiving the fluid to cause the first and second sections to move apart and increase the length of the elongated member. The device may include multiple expansion chambers along the length, and the elongated member may include multiple sections.

5 Claims, 7 Drawing Sheets

ELONGATED MEMBERS WITH EXPANSION CHAMBERS FOR TREATING BONY MEMBERS

BACKGROUND

The present application is directed to elongated members with adjustable lengths for treating bony members and, more particularly, to elongated members with one or more expansion chambers that are expandable for adjusting a length of the elongated members.

Elongated members are attached to bony members in a variety of medical situations. Examples include but are not limited to treatment of a bony member fractures, treatment of congenital deformities, limb length inequalities, traumatic bone defects, mal-alignments of the skeleton and thoracic insufficiency syndrome.

Elongated members are used extensively in the surgical treatment of spinal disorders such as degenerative disc disease, disc herniations, scoliosis or other curvature abnormalities, and fractures. The elongated members are used in a variety of different surgical treatments. In some cases, spinal fusion is indicated to inhibit relative motion between vertebral members. In other cases, dynamic implants are used to preserve motion between vertebral members. For either type of surgical treatment, elongated members may be attached to the exterior of two or more vertebral members, whether it is at a posterior, anterior, or lateral side of the vertebral members. In other embodiments, elongated members are attached to the vertebral members without the use of dynamic implants or spinal fusion.

It may be advantageous in some contexts for the elongated members to include an adjustable length. This adjustment may accommodate a patient that has grown since the elongated member was initially installed. The adjustment may also allow for adjusting the forces that the elongated members apply to the bony members.

SUMMARY

The present application is directed to devices with expandable lengths for treating bony members. In one embodiment, the device includes an elongated member with two sections that are movable relative to each other. An expansion chamber may be positioned between the first and second sections. A pump may move fluid from a reservoir and through a conduit into the expansion chamber. The expansion chamber expands upon receiving the fluid to cause the first and second sections to move apart and increase the length of the elongated member. The device may include multiple expansion chambers along the length, and the elongated member may include multiple sections.

The various aspects of the various embodiments may be used alone or in any combination, as is desired.

DETAILED DESCRIPTION

Figure 1:
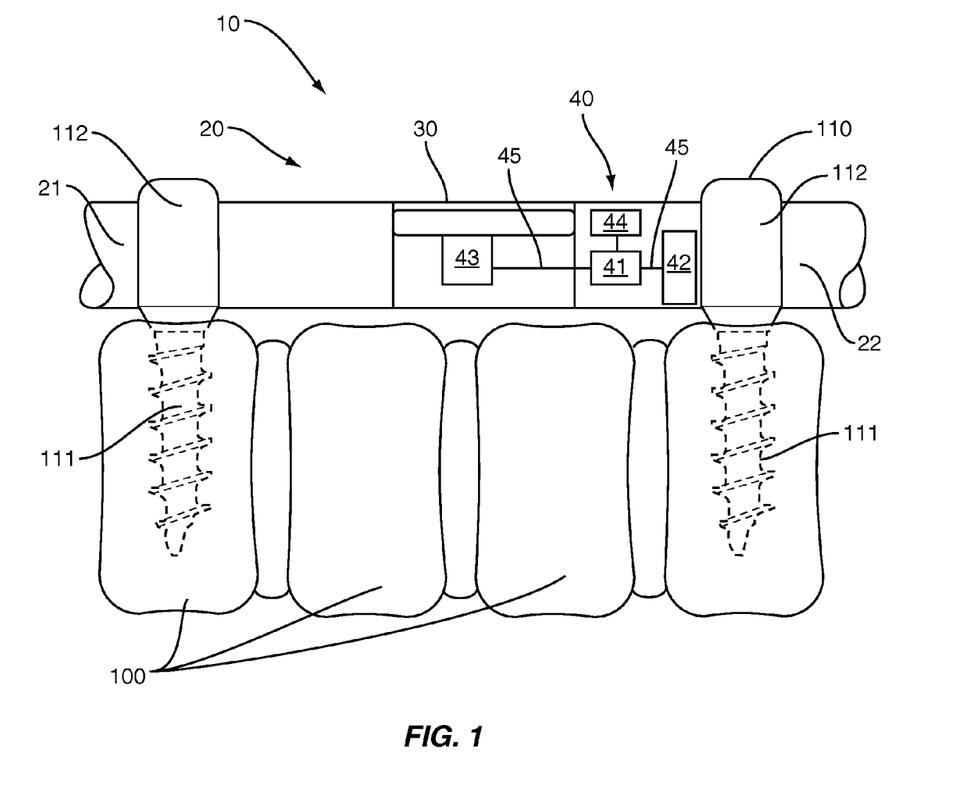
FIG. 1 is a schematic view of an expansion device according to one embodiment.

FIG. 1 schematically illustrates one embodiment of an expandable device 10 that includes an elongated member 20 with first and second sections 21, 22, an intermediate section 30, and a fluid system 40. The fluid system 40 can be activated to adjust a length of the elongated member 20. The elongated member 20 may be attached by anchors 110 to bony members 100 within a patient and can be adjusted post-operatively through the fluid system 40 to apply various corrective forces.

Figure 2:
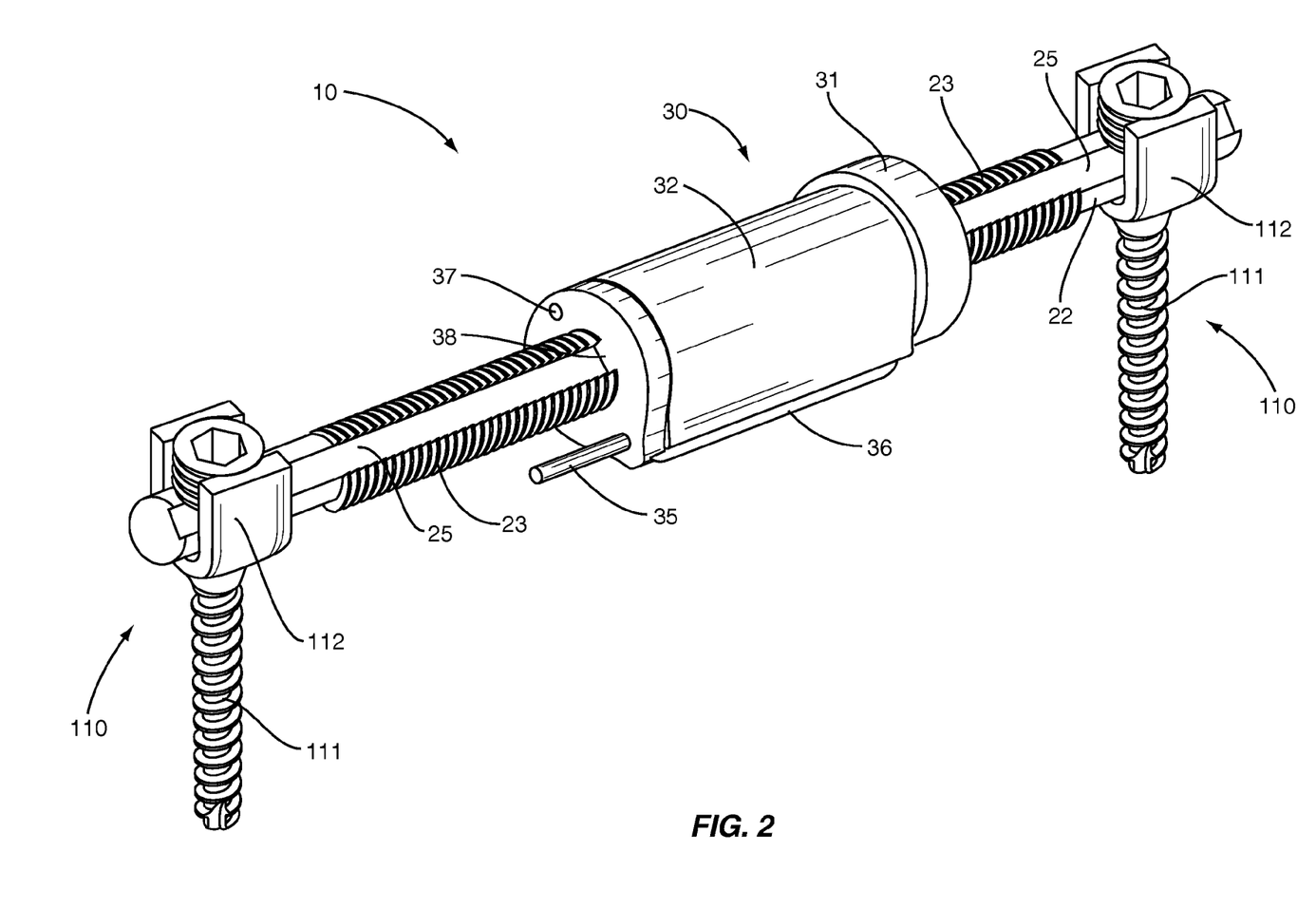
FIG. 2 is a perspective view of an expansion device according to one embodiment.
Figure 3:
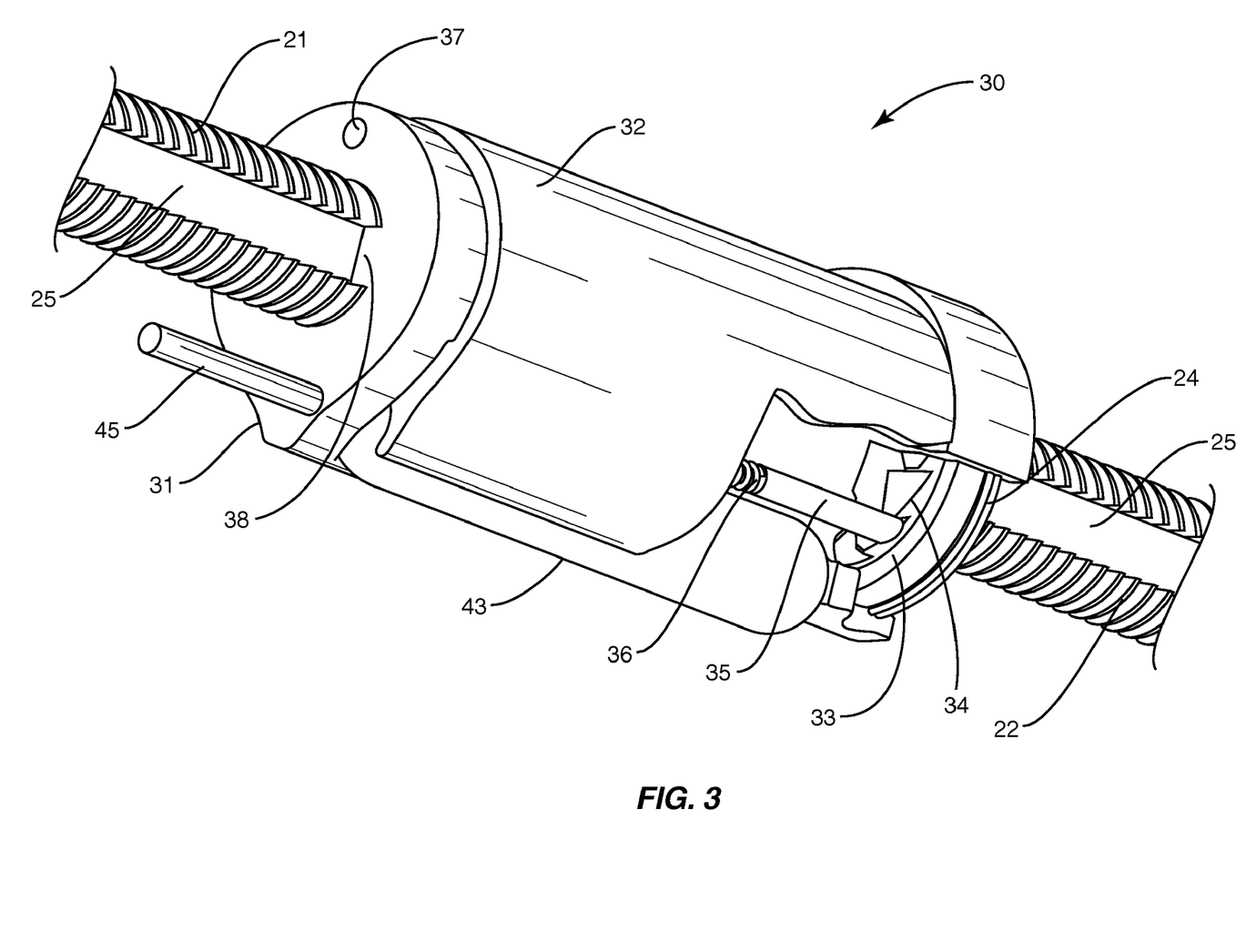
FIG. 3 is a partially cut-out perspective view of the expansion device of FIG. 2.

The device 10 may include two or more sections that are movable relative to each other to expand the device length. FIG. 2 illustrates an embodiment of the device 10 with elongated first and second sections 21, 22. The sections 21, 22 may include a variety of shapes, sizes, and physical properties depending upon the context of use. The sections 21, 22 may be substantially identical, or may include different characteristics. The embodiment of FIG. 2 includes each of the sections 21, 22 being substantially straight with a circular cross-sectional shape. In other embodiments, one or both sections 21, 22 may include a continuous curve, or include one or more discrete curved sections, and may include various cross-sectional shapes. Threads 23 may extend along a length of one or both sections 21, 22 to facilitate adjustment of the length. The sections 21, 22 may be constructed from a variety of surgical grade materials. Examples include but are not limited to stainless steels, cobalt-chrome, titanium, shape memory alloys, and polymers such as PEEK and UHMWPE.

The embodiments of FIGS. 1 and 2 include the sections 21, 22 being collinear. Sections 21, 22 may be disposed relative to each other at a variety of other orientations, including but not limited to side-by-side and overlapping. In the various orientations, the sections 21, 22 are arranged such that they can move relative to each other. This movement is generally in outward and inward directions that adjusts a length of the device 10. Outward movement causes the sections 21, 22 to move apart from one another and increase the length, while inward movement causes the sections to be in closer proximity and decrease the length.

Various anchors 110 may be used to attach the sections 21, 22 to the bony members 100. Each anchor 110 may include a shaft 111 that extends into the bony member 100. Shaft 111 may further include threads to facilitate insertion and attachment with the bony member 100. An adhesive may be placed on the shaft 111 to increase the attachment with the bony member 100. In one embodiment, the shaft 111 is coated with any number of osteoinductive or osteoconductive materials to enhance attachment as desired. Anchors 111 also include a head 112 that extends outward from the shaft 111 and is constructed to receive the sections 21, 22. The heads 112 may each include a channel sized to receive the sections 21, 22. The anchors 110 may prevent relative movement between the head 112 and the sections 21, 22, or may allow the sections 21, 22 to move relative to the heads 112. A fastener 113 may attach to each of the heads 112 to maintain the sections 21, 22 in the channels.

The sections 21, 22 are operatively connected within the intermediate section 30. In one embodiment, the sections 21, 22 are spaced apart and the intermediate section 30 acts as a connector. In another embodiment, the sections 21, 22 directly connect together within the intermediate section 30.

FIGS. 2, 3, 4A, and 4B illustrate an intermediate section 30 that connects the sections 21, 22 together. The intermediate section 30 includes a body 31 with a length to extend to each section 21, 22. An actuator 32 is pivotally connected to the body 31 along axis 37. A rotatable disc 33 with a plurality of teeth 34 arranged in an annular orientation is positioned within the body 31. A second end of the disc 33 opposite from the plurality of teeth 34 is substantially smooth and contacts against a flange 24 at the end of section 22. A pin 35 extends outward from the actuator 32 and is forced into contact with the teeth 34 by a biasing member 36.

Figure 4A:
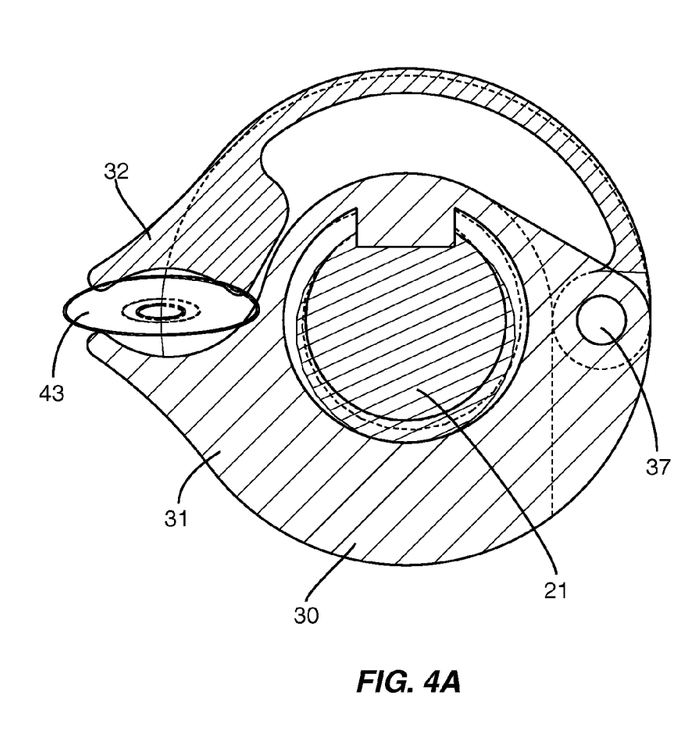
FIG. 4A is a sectional view of an expansion chamber in a contracted position according to one embodiment.
Figure 4B:
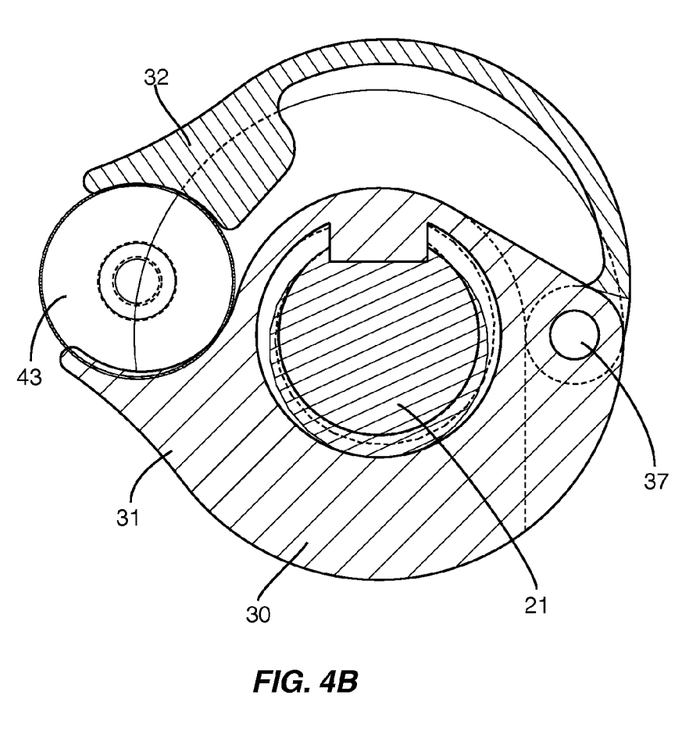
FIG. 4B is a sectional view of an expansion chamber in an expanded position according to one embodiment.

In use, fluid is moved into the expansion chamber 43 causing the chamber 43 to expand in size from a first size illustrated in FIG. 4A to an enlarged size as illustrated in FIG. 4B. Expansion of the expansion chamber 43 causes the actuator 32 to pivot about the axis 37. This movement causes the pin 35 to engage with one of the teeth 34 and to rotate the disc 33. The disc 33 is threaded onto an end of section 21 and rotatable relative to the body 31. Therefore, rotation of the disc 33 causes the section 21 to move outward away from the intermediate section 30 and thus increase a length of the device 10.

Each movement of the expansion chamber 43 from the first size to the expanded second size results in a known lengthening of the device 10. Therefore, the expansion chamber 43 may be expanded and contracted numerous times depending upon the desired length of the device 10. During contraction, the actuator 32 pivots back towards the body 31 as illustrated in FIG. 4A. This movement causes the pin 35 to slide across the toothed surface of the disc 33. The slope of the teeth 34 cause the pin 35 to slide across one or more teeth 34 depending upon the amount of rotation. The biasing member 36 maintains the pin 35 in contact with the teeth 34 to allow engagement during the next expansion cycle.

In the illustrated embodiment, the body 31 remains stationary relative to the sections 21, 22. Each end of the body 31 includes openings through which the respective section 21, 22 extends into the body interior. The openings may include tabs 38 that are positioned in longitudinal grooves 25 that extend along the sections 21, 22. The tabs 38 and grooves 25 prevent the body 21 from rotating relative to the sections 21, 22 during expansion and contraction of the expansion chamber 43.

Figure 5:
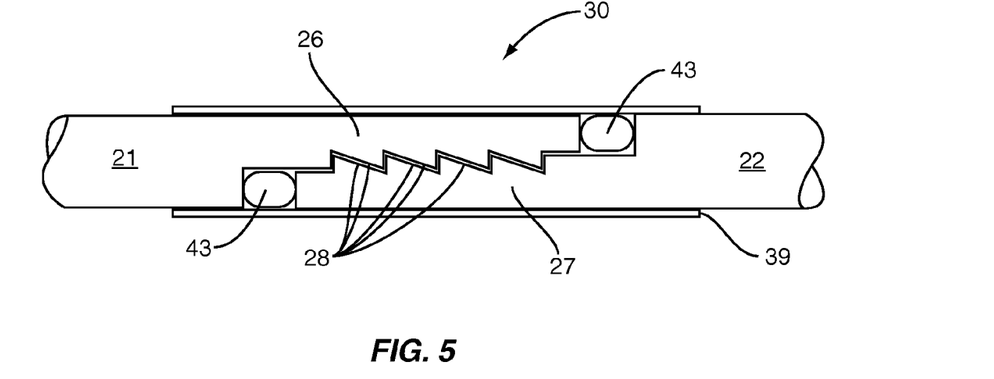
FIG. 5 is a schematic partial side view of an expansion device according to one embodiment.

FIG. 5 includes an embodiment with the sections 21, 22 directly making contact and being connected together at the intermediate section 30. Extensions 26, 27 extend outward from the facing ends of the sections 21, 22. In one embodiment, each extension 26, 27 is integrally formed with its respective section 21, 22 such that each is a unitary, one-piece construction. In another embodiment, the extensions 26, 27 are connected to its respective sections 21, 22 such as by mechanical fasteners, adhesives, and welding. Each extension 26, 27 includes teeth 28 that are oriented to allow the sections 21, 22 to slide apart, but prevent the sections 21, 22 from moving together. One or more of the teeth 28 and/or sections 26, 27 may be flexible to allow for deformation as the teeth 28 move across each other as the sections 21, 22 separate apart.

The intermediate section 30 may also include a sleeve 39 that extends between the sections 21, 22. The sleeve 39 is hollow to extend over the ends of the sections 21, 22. The sleeve 39 may be constructed from an expandable material to accommodate outward movement of the sections 21, 22. In one embodiment, sleeve 39 includes excess length that may be in the form of folds, pleats, and the like to provide for the outward movement of the sections 21, 22. The sleeve 39 may also provide shield to prevent bodily materials from accessing the interior of the intermediate section 30 which may prevent movement of the sections 21, 22, or proper functioning of the fluid system 40.

Figure 6:
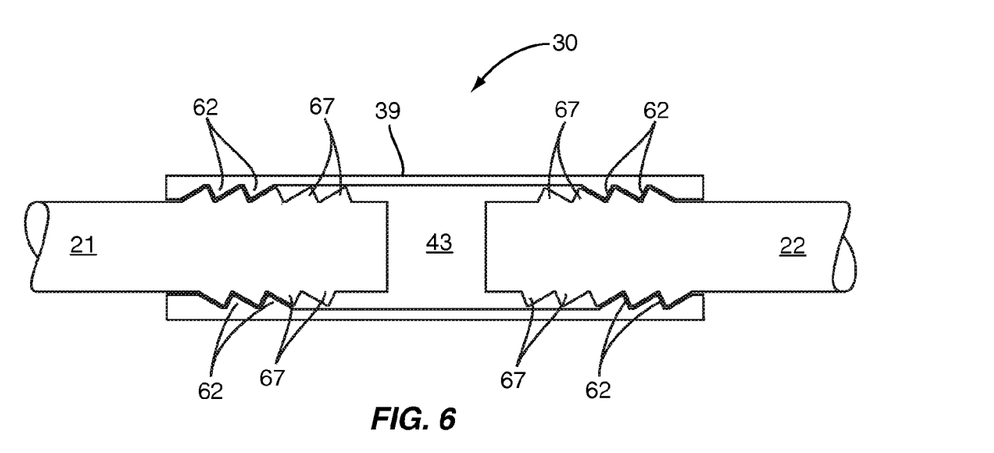
FIG. 6 is a schematic partial side view of an expansion device according to one embodiment.

Sleeve 39 may also facilitate the positioning of the device 10. FIG. 6 includes an embodiment with the sleeve 39 including teeth 62 that engage with teeth 67 on the sections 21, 22. The teeth 62, 67 may be angled to allow movement of the sections 21, 22 in a first direction, and prevent movement in the second opposite direction.

The fluid system 40 provides the force for adjusting the length of the expansion device 10. The fluid system 40 may include one or more expansion chambers 43 that interact with the elongated member 20, one or more reservoirs 42 that contain fluid that is moved into the expansion chambers 43, one or more pumps 41 that moves the fluid between the reservoirs 42 and expansion chambers 43, one or more conduits 45, and one or more power sources 44 to drive the pump 41. The fluid system 40 is a closed system as the fluid remains contained within the various elements and is not released into the patient.

The expansion chamber 43 is able to receive the fluid and interact with the elongated member 20. It may not be necessary for the fluid to completely fill or be completely removed for the expansion chamber 43 to function and adjust the length of the device 10.

In one embodiment, the expansion chamber 43 is a separate member that is capable of containing the pressurized fluid, and selectively positionable between a first contracted size when the fluid is removed and a second expanded size when containing the fluid. The expansion chamber 43 is constructed of an expandable material that expands and contracts due to the position of the fluid. The expansion chamber 43 may be constructed from various materials including but not limited to rubber and plastic. The expansion chamber 43 may also be constructed from non-expandable materials such as various metals that are mechanically formed to allow expansion and contraction, such as a bellows arrangement.

The expansion chamber 43 may not be a separate member, but rather is formed between other elements of the device 10. FIG. 6 includes an embodiment with the expansion chamber 43 formed between the ends of the sections 21, 22, and the sleeve 39.

In the various embodiments, the expansion chambers 43 include an inlet to receive the fluid. A separate outlet may also be included within the expansion chambers 43, or the inlet may also be utilized for removing the fluid. The expansion chambers 43 may include a single internal chamber that contains the fluid, or may include two or more chambers that are fluidly connected together.

The reservoir 42 contains the fluid that is moved to and from the expansion chamber 43. The reservoir 42 may include the same or different fluid capacity than the expansion chamber 43. The size of the reservoir 42 may be constant, or the size may vary depending upon the amount of contained fluid. In one embodiment, the fluid system 40 includes multiple reservoirs for moving fluid to and from the one or more expansion chambers 43.

The pump 41 moves the fluid between the expansion chamber 43 and the reservoir 42. In one embodiment, the pump 41 includes a first port that leads to/from the expansion chamber 43, and a second port that leads to/from the reservoir 42. In one embodiment, the pump 41 operates in first and second directions. In a first direction, fluid is moved from the reservoir 42 and into the expansion chamber 43. In the second direction, the fluid is moved from the expansion chamber 43 and into the reservoir 42.

Figure 7:
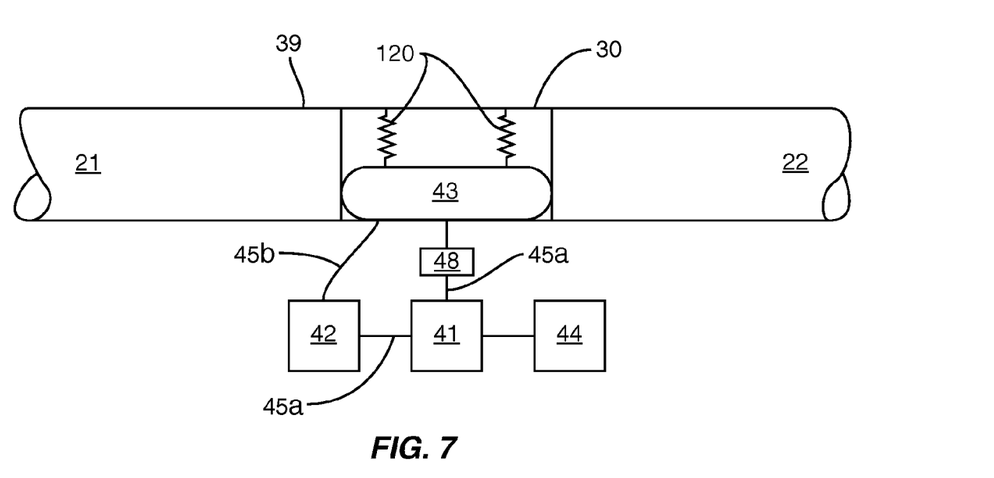
FIG. 7 is a schematic partial side view of an expansion device according to one embodiment.

FIG. 7 includes an embodiment in which the pump 41 operates in just one direction. In this embodiment, pump 41 operates to move the fluid from the reservoir 42 and through the conduit 45a into the expansion chamber 43. The expansion chamber 43 is positioned to contact against one or more biasing members 120. During expansion, the pump 41 overcomes the force applied by the biasing members 120 to move the fluid into the expansion chamber 43. Once the pump 41 stops, the biasing members 120 contact the expansion chamber 43 and force the fluid into the conduit 45b and back into the reservoir 42. The conduit 45a and/or pump 41 may include a valve 48 to prevent fluid flow from the expansion chamber 43.

A power source 44 supplies power to the pump 41 for moving the fluid between the various elements. In one embodiment, the power source includes one or more batteries. Other embodiments of power sources 44 include a captured-magnet arrangement, and an osmotic pressure gradient arrangement.

Various types of fluid may be used for inflating the expansion chamber 43. The fluid may be a hydraulic fluid or a gas fluid. Examples include but are not limited to saline, and air.

In some embodiments, the entire fluid system 40 may be contained within the elongated member 20, within the intermediate section 30, or within a combination of the elongated member 20 and the intermediate section 30. FIG. 1 illustrates one such embodiment with the fluid system 40 contained within the interior of the elongated member 20 and intermediate section 30. Positioning the fluid system 40 within the interior may reduce the overall size of the expandable device 10 and allow for the device 10 to be used in more contexts. Also, the elongated member 20 and intermediate section 30 may protect the fluid system 40 and may also form a shield from bodily fluid and tissue growth that may cause adverse affects over time after the device 10 is implanted within the patient.

In other embodiment, a portion of the fluid system 40 is positioned on the exterior of the elongated member 20 and intermediate section 30. FIG. 7 includes an embodiment with the pump 41, reservoir 42, and power source 44 positioned on the exterior. This may facilitate accessing and maintaining these elements, or replacing one of the elements, such as the power source 44 that comprises a battery.

In one embodiment, the fluid system 40 does not include a power source 44. Instead, the fluid system 40 may be connected to a separate power source, such as during examination by a doctor. The fluid system 40 may then be activated at this time while under supervision of the doctor.

Figure 9:
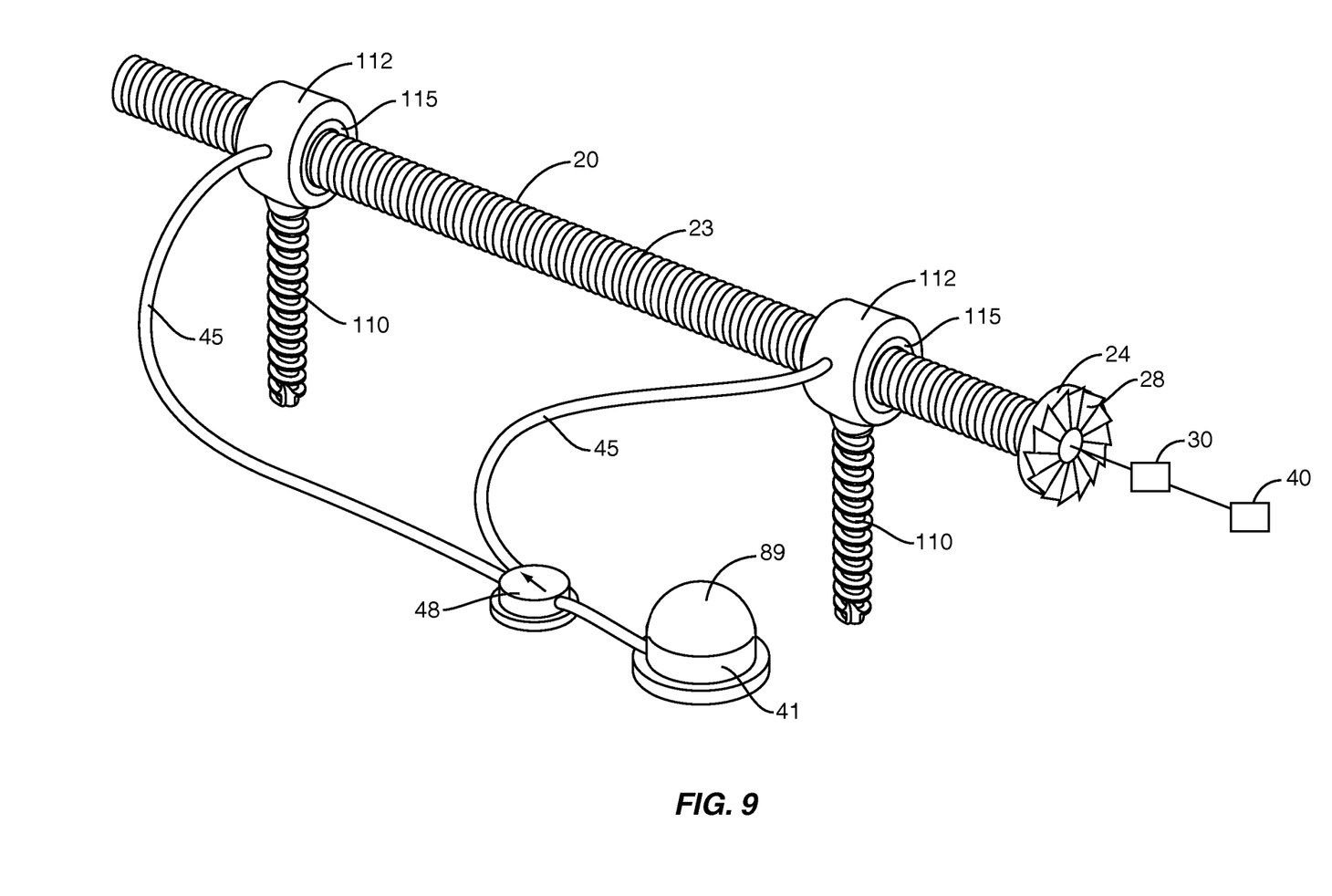
FIG. 9 is a perspective view of adjustable anchors positioned along a length of an elongated member according to one embodiment.

In one embodiment, the fluid system 40 does not include a power source 44 per se but rather uses manual force supplied by a person, such as the patient or doctor. FIG. 9 includes one embodiment that the pump 41 is a compressible bulb 89. The bulb 89 is positioned in a location for the person to apply a force and compress the bulb 89 to force the fluid within the system 40. The bulb 89 may be attached to a bony member 100 that provides a stable base such that the user may compress the bulb 89. One similar type of bulb embodiment is available in the STRATA Shunt Assembly available from Medtronic, Inc.

When the device 10 is implanted within the patient, the elongated members 20 and intermediate section 30 are attached to the bony members 100. In one embodiment, the entire device 10 is subcutaneous. Activation of the fluid system 40 may occur remotely, such as through a wireless transmitter. In other embodiments, elements of the fluid system 40, such as the power source 44 and/or pump 41 may be exposed above the skin. This provides access to these elements for maintenance, replacement, and activation of the fluid system 40.

In one embodiment, one or more elements of the fluid system 40 may be removable. By way of example, the power source 44 and pump 41 may be removable. These elements may not be connected until it is necessary to adjust the length of the device 10. In this manner, the device 10 may be less cumbersome to the patient.

Figure 8:
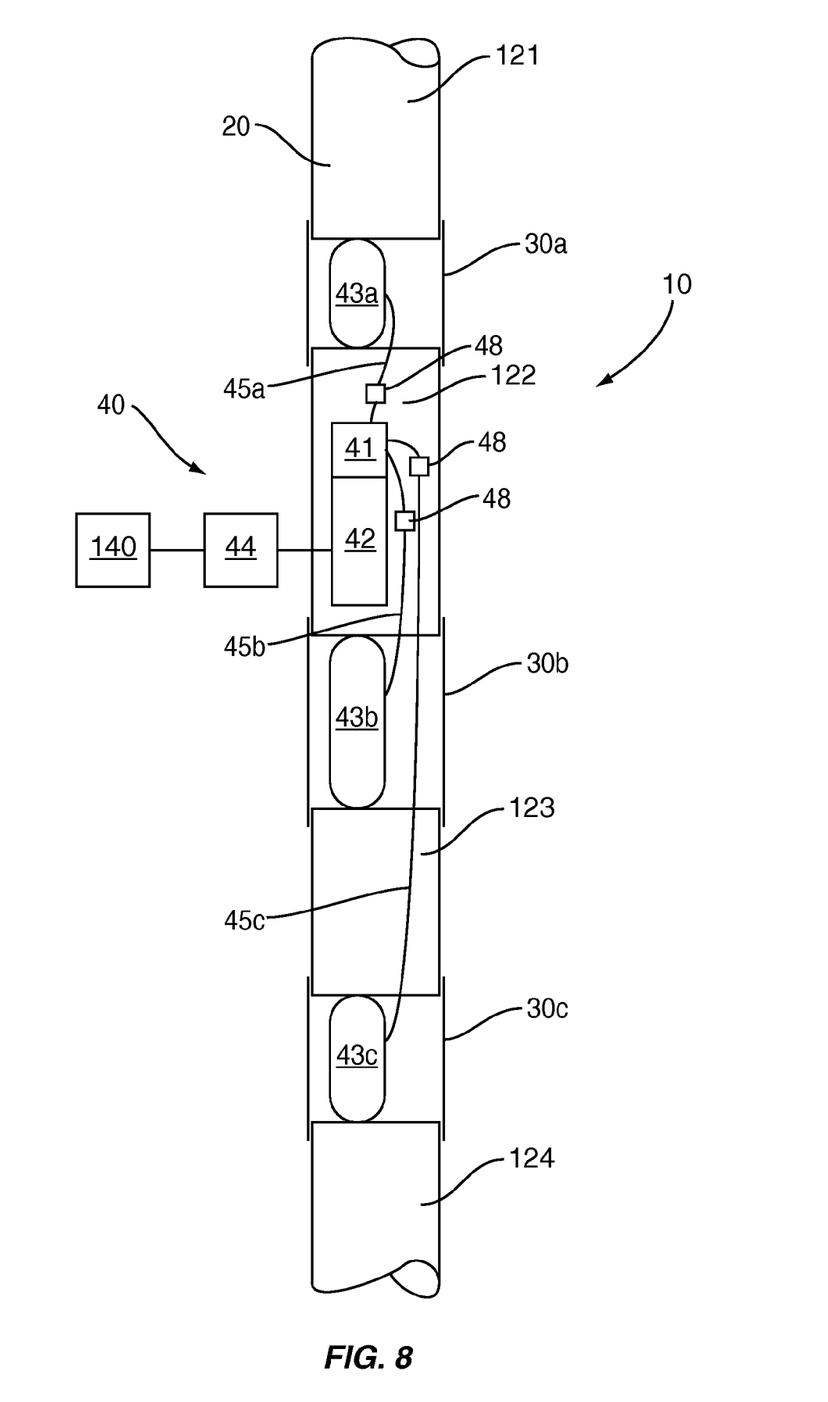
FIG. 8 is a schematic partial side view of an expansion device according to one embodiment.

The fluid system 40 may be implemented to control the expansion at a single point along the elongated member 20. In other embodiments, the fluid system 40 may control the distraction at two or more points along the elongated member 20. FIG. 8 includes an embodiment that the fluid system 40 controls the length at three points spaced along the elongated member 20. The fluid system 40 includes a reservoir 42, pump 41, and power source 44, and three expansion chambers 43a, 43b, 43c. Expansion chamber 43a is positioned between sections 121 and 122, expansion chamber 43b between sections 122 and 123, and expansion chamber 43c between sections 123 and 124. Sections 121, 122, 123, and 124 are the same as previously explained above for sections 21 and 22.

The pump 41 moves fluid from the reservoir 42 into each of the expansion chambers 43a, 43b, 43c. The pump 41 may be capable of operating in one direction and relies on another mechanism to return the fluid to the reservoir 42, or the pump 41 may operate in two directions and is able itself to pump the fluid back into the reservoir 42. The fluid system 40 may be configured such that each of the expansion chambers 43a, 43b, 43c can be independently operated. Valves 48 may be positioned along the conduits 45a, 45b, 45c that lead between the reservoir 42 and the respective expansion chambers 43a, 43b, 43c. The valves 48 may be turned on and off to control the flow of the fluid and the expansion of the appropriate expansion chamber 43a, 43b, 43c.

In one embodiment, the amount of fluid contained in the reservoir 42 is adequate to simultaneously operate each of the expansion chambers 43a, 43b, 43c. Therefore, the elongated member 20 can simultaneously expand at three different sections at the same time. In another embodiment, the amount of fluid in the reservoir 42 is only adequate to operate one expansion chamber 43a, 43b, 43c. Therefore, two of the expansion chambers 43a, 43b, 43c are idle while the pump 41 moves the fluid from the reservoir 42 and into the selected chamber. In other embodiments, the amount of fluid may be adequate to operate more than one chamber, but not all chambers simultaneously.

A controller 140 may be operatively connected to the fluid system 40 to control the fluid flow. In one embodiment, controller 140 includes a microprocessor, random access memory, read only memory, and an input/output configuration. Controller 140 may include programming stored within the memory or is able to receive commands to adjust the length of the expandable device 10 accordingly. Controller 140 may operate the pump 41 and valves 48 to control the timing and amount of the expansion/contraction. Controller 140 may also store the length of the device 10 and provide this information to the patient and/or doctor.

In one embodiment, the body 30 rotates around the elongated member 20 to control the length of the device 10. In another embodiment, the elongated member 20 rotates as the body 30 may remain relatively stationary. FIG. 9 includes one embodiment with the body 30 is positioned at an end of the elongated member 20. The body 30 may be secured to prevent rotation. In one embodiment, the body 30 is secured with an anchor. The body 30 includes a mechanism, such as that illustrated in FIG. 3, that engages with teeth 34 positioned on a flange 24 at an end of the elongated member 20. A fluid system 40 causes the body 30 to engage and rotate the elongated member 20.

One or more anchors 110 are spaced along the length of the elongated member 20. Each anchor 110 includes an expansion chamber (not illustrated) positioned within the head 112, and a nut 115 that engages with threads 23 on the elongated member 20. Each expansion chamber 43 is able to receive fluid forced by a pump 41 through a conduit 45. A valve 48 may be positioned along the conduit 45 to control the flow of the fluid.

When fluid is forced into the expansion chamber 43, the expansion chamber 43 expands and prevents rotation of the nut 115 positioned in the head 112. When the nut 115 rotates, there is no relative movement between the elongated member 20 and the anchor 110. Conversely, when the nut 115 is held stationary, the elongated member 20 moves relative to the anchor 110. Therefore, the force applied by the device 10 can be tailored to specific sections along the length of the elongated member 20.

The embodiment of FIG. 9 includes a separate pump 41 for moving fluid to the anchors 115. In another embodiment, the fluid system 40 provides the fluid for adjusting the nuts 115 in the anchors 110.

A variety of bony members 100 may be treated by the expandable device 10. FIG. 1 includes the bony members 100 comprising vertebral members that form a section of the spine. Another embodiment includes a fractured bone, such as the tibia or femur.

In some embodiments, the reservoir 42 is a separate element from the pump 41. In other embodiments, the two elements are included in the same device. By way of example, the pump 41 in FIG. 9 functions as both the pump 41 both to move the fluid to and from the anchors 115, and as the reservoir to store the fluid within the bulb 89.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The methods and devices disclosed herein may be carried out in other specific ways than those herein set forth without departing from the scope and essential characteristics of the application. In embodiments with multiple expansion chambers 43, the expansion chambers 43 may be the same or different. The present embodiments are, therefore, to be considered in all respects as illustrative and not restrictive, and all changes coming within the meaning and equivalency range of the appended claims are intended to be embraced therein.

What is claimed is:

1. An expandable device to treat bony members comprising:
   an elongated member configured to attach to the bony members with a length measured along a longitudinal axis, the elongated member including first and second sections that are collinear, the first and second sections being configured so that both sections move either apart from one another, or toward one another;
   an intermediate section positioned between and collinear with the first and second sections, the intermediate section comprising a body having a length extending to each first and second section, and an actuator pivotally connected to the body along an axis;
   an expansion chamber positioned between the first and second sections;
   a reservoir positioned within an interior of the intermediate section and spaced apart from the expansion chamber, the reservoir configured to contain a fluid;
   a conduit that extends between the expansion chamber and the reservoir;
   a pump configured to move the fluid through the conduit from the reservoir and into the expansion chamber;
   a rotatable member attached to one of the first and second sections, the rotatable member being rotated by expansion of the expansion chamber a rotatable member attached to one of the first and second sections, the rotatable member being rotated by expansion of the expansion chamber and causing separation of the first and second sections; and causing separation of the first and second sections;
   the expansion chamber being expandable upon receiving the fluid to cause the actuator to pivot about the axis, thereby causing each of the first and second sections to move apart and increase the length of the elongated member.

2. The expandable device of claim 1, wherein the reservoir, expansion chamber, and conduit form a closed system that prevents escape of the fluid.

3. The expandable device of claim 1, wherein the expansion chamber is constructed of a flexible material.

4. The expandable device of claim 1, wherein the pump is further configured to move the fluid through the conduit from the expansion chamber and into the reservoir.

5. The expandable device of claim 1, further comprising a biasing member positioned to contact against the expansion chamber and force the fluid from the expansion chamber and into the reservoir when the pump is not activated.

* * * * *